United States Patent [19]

Nikitin et al.

[11] Patent Number: 4,619,899

[45] Date of Patent: Oct. 28, 1986

[54] METHOD AND DEVICE FOR PERFORMING MICROOPERATIONS ON CELLS

[75] Inventors: Vladimir A. Nikitin; Anatoly M. Khokhlov; Vyacheslav T. Larin; Boris A. Fikhte, all of Puschino, U.S.S.R.

[73] Assignee: Institut Biokhimii I Fiziologii Mikroorganizmov Akademii Nauk SSR, Puschino, U.S.S.R.

[21] Appl. No.: 713,389

[22] PCT Filed: Jun. 30, 1983

[86] PCT No.: PCT/SU83/00023
§ 371 Date: Feb. 12, 1985
§ 102(e) Date: Feb. 12, 1985

[87] PCT Pub. No.: WO85/00314
PCT Pub. Date: Jan. 31, 1985

[51] Int. Cl.[4] .............................. C12M 1/76
[52] U.S. Cl. ......................... 435/287; 128/573; 604/176
[58] Field of Search ............. 435/287, 803, 30; 935/53, 85; 422/99, 100; 128/752, 753; 604/164, 176

[56] References Cited

FOREIGN PATENT DOCUMENTS

| 1085965 | 2/1955 | France . | |
| 76091 | 5/1983 | Japan | 935/53 |
| 69345 | 1/1948 | U.S.S.R. . | |
| 140170 | 11/1961 | U.S.S.R. . | |

*Primary Examiner*—Alan Cohan
*Attorney, Agent, or Firm*—Fleit, Jacobson, Cohn & Price

[57] ABSTRACT

A method for performing microoperations on cells consists in that a cell is secured to a micro suction cup and the cell membrane is perforated by a microinstrument. The cell membrane is pierced in a spot under the micro suction cup, the microinstrument being introduced through the recess of the micro suction cup, which is filled with an isotonic solution.

A device for performing microoperations on cells comprises a microinstrument (1) installed in a holder (2) rigidly secured to a movable tip (3) a three-way micromanipulator (4), and a micro suction cup (5). The latter is rigidly secured to the holder (2), the microinstrument (1) is located in the recess of the micro suction cup (5) coaxially therewith and is connected to the holder (2) by a means (7a) ensuring the reciprocating movement of the microinstrument (1) along the axis of the micro suction cup (5).

6 Claims, 6 Drawing Figures

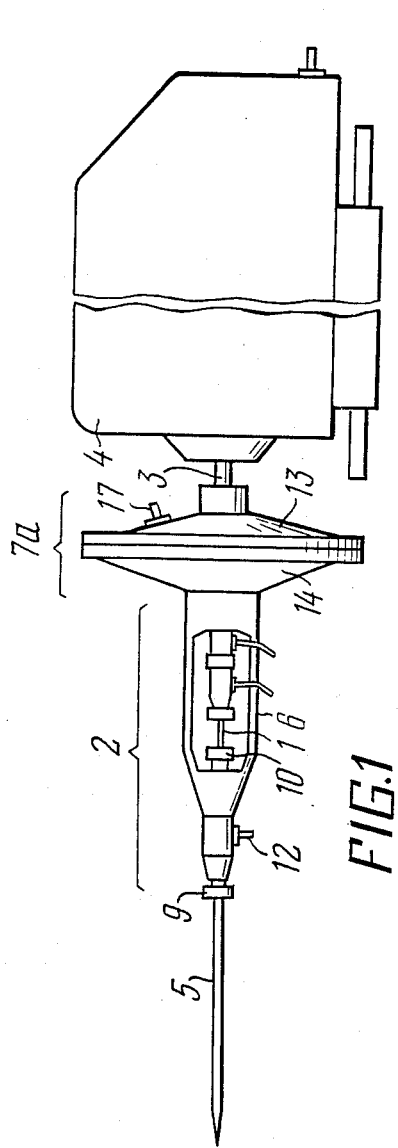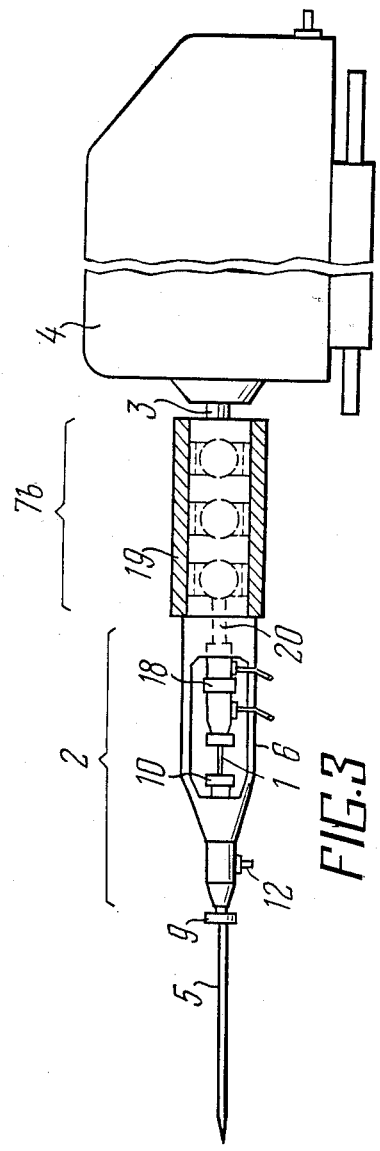

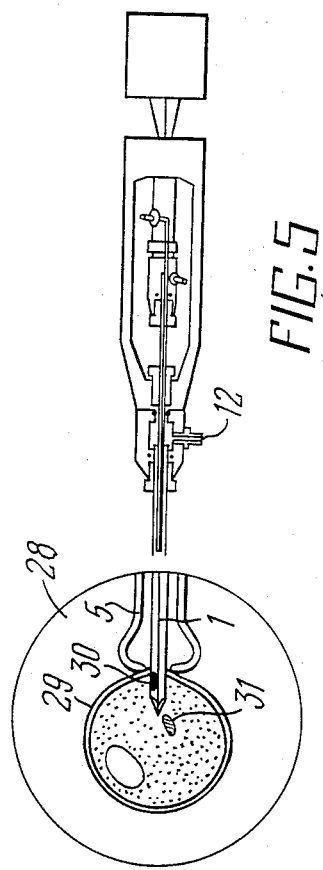
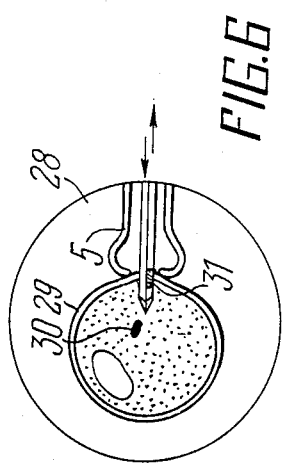
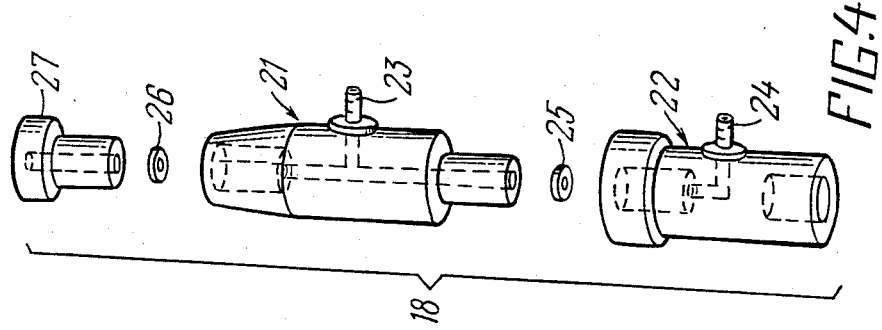

METHOD AND DEVICE FOR PERFORMING MICROOPERATIONS ON CELLS

TECHNICAL FIELD

This invention relates to biology and, in particular, to a method for performing microoperations on cells and a device therefor.

BACKGROUND ART

Known in the art is a method for performing microoperations on cells, comprising the steps of securing a cell by means of a micro suction cap and introducing a microinstrument into the cell. The cell is pierced from the side opposite to the place where it is secured (cf., for example, P. Fonbruhn, Metody Mikromanipulyatsii, Inostrannaya Literature, Moscow, pp. 147–149, 1951, in Russian).

The cell membrane is extremely tough and resilient, and cannot be pierced at once by a touch of the sharp tip of the microinstrument, but is punctured only after a substantial deformation of the cell portion to be pierced and of the whole cell. As a result the cell is seriously injured.

Moreover, large deformation of the cell during the piercing process can lead to membrane rupture and subsequent ejection, and the loss of cytoplasm due to the general increase of the intracellular pressure. In some cases even organelles can be displaced in relation to one another.

Ejection of cytoplasm results in upset of the balance between the intracellular matter and the environment, and the cells which have been operated on become less viable.

Also known in the art is a method for performing microoperations on cells, which is a method of nuclei transplantation, comprising the steps of extracting a nucleus from the recipient cell and transplanting it into the donor cell whose own nucleus had been removed.

This procedure involves two introductions of a microinstrument into a cell: the first time to remove the nucleus and the second time to place another nucleus. The cell is, therefore, injured twice.

The number of successful operations is, as a rule, rather low (cf., for example, M. U. Koras, Instrumentation for the Transplantation of Nucleoli, Journal of the Franklin Institute, 262, 407–411, 1956).

Known in the art is a device for performing microoperations on cells, comprising a microinstrument placed in a holder rigidly connected to a mobile tool of a three-way micromanipulator, and a micro suction cup fitted on another micromanipulator intended to secure the cell to be operated on (cf., for example, French Patent No. 1,085,965 published in 1965).

This device has a rather complicated system of manipulator control and relatively low productivity during microoperations, since the operation of two micromanipulators has to be matched. In addition it is expensive and can still damage the cell when piercing it. The cell is still more damaged because of the vibration of the micro suction cup and microinstrument. Since the cell attached to the micro suction cup is sufficiently resilient, the microinstrument can be broken in an attempt to pierce the cell.

DISCLOSURE OF THE INVENTION

The invention is to provide an improved method for performing microoperations on cells so as to minimize the deformation of the cell when it is perforated and increase the number of successful operations, and also to provide a device to realize this method, which should be convenient in operation, inexpensive, sufficiently reliable, and efficient enough to cut down the time of microoperations.

There is provided a method for performing microoperations on cells, comprising the steps of securing a cell by means of a micro suction cup, and perforating the cell membrane by a microinstrument, in which, according to the invention, the cell membrane is pierced in the spot under the micro suction cup, the microinstrument being introduced through the recess of the micro suction cup.

The recess of the micro suction cup should be preferably filled with an isotonic solution.

There is also provided a device for performing microoperations on cells, comprising a microinstrument fitted in a holder rigidly connected to a mobile tool of a three-way micromanipulator, and a micro suction cup to secure the cell to be operated on, in which, according to the invention, the micro suction cup is rigidly secured to the holder of the microinstrument which is located in the recess of the micro suction cup coaxially therewith and connected to the holder by a device enabling the microinstrument to move reciprocally along the axis of the micro suction cup.

The holder should preferably be made as a hollow tee-joint whose one pipe communicates with the recess of the micro suction cup, the opposite pipe features a sealing ring having an opening fitting the diameter of the microinstrument, while the third lateral pipe is equipped with a nipple in order to produce a negative pressure in the micro suction cup recess and to provide an input for the isotonic solution.

The microinstrument should preferably be connected to the holder by a lengthwise stepping mechanism or a diaphragm box whose case is rigidly secured to the holder, while the diaphragm is rigidly secured to the microinstrument, the chamber of the box being communicated with a source of control pneumatic impulses.

The method for performing microoperations on cells, according to the invention, provides for:

elimination of the cell deformation, when a microinstrument pierces the cell;

lesser cell damage;

high precision of introduction of the microinstrument inside the cell to a specific depth;

penetration of the microinstrument into any cell, whatever its shape and size;

displacement of the cell, if necessary, together with the introduced microinstrument;

a single-puncture transplantation of the cell organelles;

microinjection of substances into specific cell portions or individual cell organelles;

a faster microsurgery process.

The device for performing microoperations on cells, according to the invention, provides, in addition to the advantages inherent in the method, for high reliability, simplicity of control since only one micromanipulator is to be operated, a lower price as compared to prior art devices, and less likelihood of breaking a microinstrument when piercing the cell.

BRIEF DESCRIPTION OF THE DRAWINGS

The invention will now be described in more detail with reference to specific embodiments thereof and accompanying drawings, wherein:

FIG. 1 shows a general view of a device for performing microoperations on cells;

FIG. 3 shows the view of FIG. 1 with a stepping mechanism;

FIG. 4 shows a fragmentary view of an embodiment of a holder for a double-passage microinstrument;

FIG. 5 shows a schematic of a device for performing microoperations on cells and a cell, as seen in the microscope, when the microinstrument is introduced into the cell;

FIG. 6 shows a cell, as seen in the microscope, when the microinstrument is retracted therefrom.

BEST MODE FOR CARRYING OUT THE INVENTION

Figure 2:
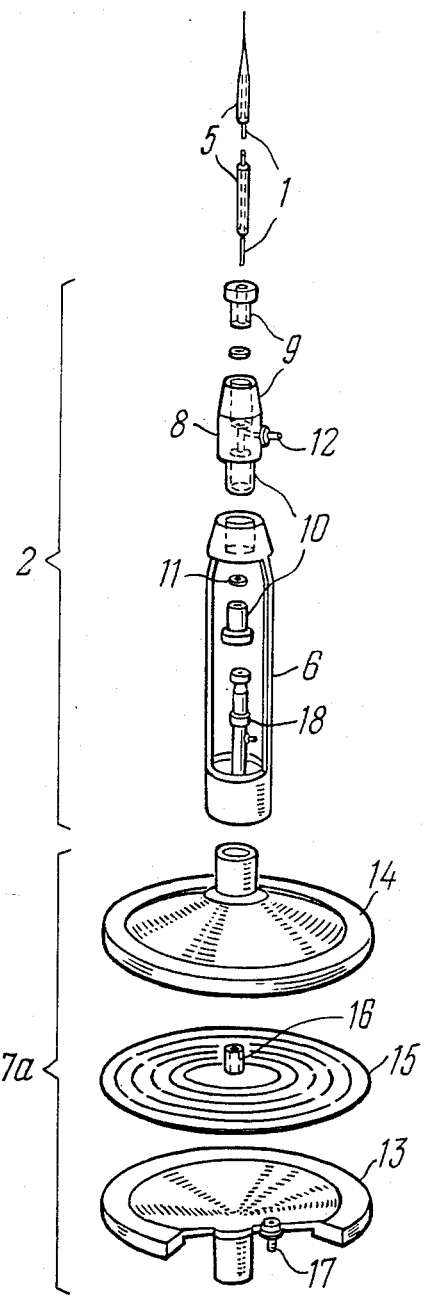
FIG. 2 shows a fragmentary view of a micro suction cup and a microinstrument with a diaphragm box.

A method for performing microoperations on cells, according to the invention, consists in that a cell with is to be subjected to microsurgery is secured by means of a micro suction cup. The cell is secured by a negative pressure produced in the recess of the micro suction cup through a microinjector after the cell is brought into contact with the butt end of the micro suction cup. The cell membrane is pierced by a microinstrument within a spot limited by the butt end of the micro suction cup, and the microinstrument is introduced into the cell from the recess of the micro suction cup. The immobilized and stretched-out membrane portion under the micro suction cup is washed with an isotonic solution which fills the recess of the micro suction cup prior to the operation. The isotonic solution is introduced into the micro suction cup in order to maintain, at the moment the membrane is punctured, the balance of the osmotic pressure of the intercellular matter and the extracellular solution in the zone of the cell membrane puncture. The Ringer solution is used as an isotonic solution for cells of cold-blooded animals, protozoa and microorganisms, and Ringer-Locke, Ringer-Tirode and other solutions for cells of warm-blooded animals. Calcium iones should be present as the membrane stabilizing agent in all these solutions so that the damaged portion of the membrane could be quickly restored. In some cases, when transplanting whole intracellular organelles, for example, where large-diameter microinstruments are required and the cell membrane is, therefore, seriously damaged, the isotonic solution contains, as a rule, high-molecular compounds, such as collidine, dextran and the like, in order to produce a colloidal-osmotic or oncotic pressure which is due to the presence, in the cell cytoplasm, of high-molecular, mainly proteic, substances. All this contributes to a fast restoration of the perforated cell membrane and insignificant loss of intracellular components passing into the recess of the micro suction cup during perforation.

The method for performing microoperations on cells, according to the present invention, is remarkable in that the cell is not deformed at all during perforation because it is held and pierced by a microinstrument only in the area of the membrane which is immobilized and stretched out by the tip of the micro suction cup. This portion of the cell membrane is easily perforated by a microinstrument, while the cell is not affected in any way and is not subjected to deformation.

The use of the proposed method makes the process of cell microsurgery much faster since it eliminates an extremely troublesome and time-consuming search for a perforation spot. Such a spot is determined by the way the cell is attached to the micro suction cup. Moreover, the micro suction cup and the microinstrument are manipulated simultaneously. The microinstrument cannot slide off the membrane during perforation and is, therefore, introduced into the cell very precisely irrespective of the cell shape and size.

The method for performing microoperations on cells, according to the invention, is realized by a device shown in FIGS. 1, 2, 3 and 4.

Referring to FIG. 1, a device for performing microoperations on cells, comprises a microinstrument 1 installed in a holder 2 rigidly connected with a movable tip 3 of a three-way micromanipulator 4, and a micro suction cup 5 which is rigidly secured in the holder 2. The microinstrument 1 is located in the recess of the micro suction cup 5 coaxially therewith and is connected to the holder 2 by a casing 6 and a means 7a (FIGS. 1 and 2) for reciprocal motion of the microinstrument 1 along the axis of the micro suction cup 5.

The holder 2 whose fragmented view is shown in FIG. 2 is a hollow tee-joint 8 whose first pipe 9 is rigidly secured to the micro suction cup 5 and communicates with the recess of said micro suction cup 5, an opposite pipe 10 houses a sealing ring 11 having a central hole fitting the diameter of the microinstrument 1, while a third side pipe is equipped with a nipple 12 in order to produce a negative pressure in the recess of the micro suction cup 5 and to provide an input for the isotonic solution.

The means 7a is a diaphragm box comprising a casing 13 and a lid 14, and a diaphragm 15 placed between them and fitted with a plunger 16. The casing 13 has a nipple 17 through which the chamber of the diaphragm box communicates with a source of control pneumatic impulses (not shown). The diaphragm 15 is rigidly secured to the microinstrument 1 by the plunger 16 and a clamp 18.

Referring to FIG. 3, an embodiment of a device for performing microoperations on cells is provided with a means 7b, which ensures the reciprocating motion of the microinstrument 1 in the recess of the micro suction cup 5 and, unlike the means 7a of the embodiment of FIGS. 1 and 2, is a lengthwise stepping mechanism whose casing 19 is rigidly secured to the holder 2 and a movable tip 20 thereof is rigidly secured to the microinstrument 1.

Referring to FIG. 4 showing a fragmented view of an embodiment of a clamp 18 for a double-passage microinstrument, this clamp 18 comprises sectional pipes 21 and 22 equipped with nipples 23 and 24, respectively, to communicate with respective pipes of the microinstrument 1. The pipes 21 and 22 are joined together and sealed by a washer 25. The pipe 21 is also provided, on its free end, with a sealing washer 26 with a lock-nut 27.

The device of FIGS. 1 through 4 operates as illustrated in FIGS. 5 and 6, using an example of transplantation of neclei, and goes on as follows.

Using the micromanipulator 4 (FIG. 1), the microinstrument 1 and the micro suction cup 5 are brought into the field 28 (FIG. 5) of vision of the microscope near a cell 29. A separate microinjector connected to the nipple 12 (FIG. 1) is used to provide rarefaction. The tip of the micro suction cup 5 is brought to the cell 29 (FIG. 5) so that it is sucked to the end of the micro suction cup 5. The portion of the cell membrane limited by the cup is the spot where the microinstrument 1 is introduced into the cell 29. Then the pressure is supplied through the nipple 17 (FIG. 1) into the chamber of the diaphragm box or into the chamber of the stepping mechanism 7b (FIG. 3). The diaphragm 15 (FIG. 2) is subjected to deformation and pushes the plunger 16 and the clamp 18 holding the microinstrument 1. In the embodiment equipped with a stepping mechanism, the movable tip 20 (FIG. 3) pushes the microinstrument 1. The microinstrument 1 moves forward and perforates the membrane portion immobilized and limited by the diameter of the microsuction cup 5 (FIG. 5). A nucleus 30 taken from another cell is at first placed in one of the pipes of the microinstrument 1. In this case the microinstrument 1 is a double-passage pipette, each passage thereof being connected to respective microinjectors which are to suck in and push out the nuclei. Both operations are performed through the microinstrument 1 by supplying pressure or rarefaction inside the holder 2 (FIG. 4) along two passages through the nipples 23 and 24 (FIG. 4). The isotonic solution which is to reduce the damage effect of the cell membrane perforation is supplied from a microinjector (not shown) through the nipple 12 (FIG. 5). When the microinstrument 1 is inside the cell 29, a nucleus 31 (FIG. 6) is sucked into the free passage of the microinstrument 1 and the transplant nucleus 30 which is in the second passage of the microinstrument 1 is pushed inside the cell 29. This means that the nuclei transplant operation needs only one perforation to be completed.

INDUSTRIAL APPLICABILITY

The present invention can be used in the fields of biology, agriculture and medicine. It can be successfully employed for isolation and transplantation of nuclei and organelles, ovum blastomeres, microinjections of various substances into cells in order to inactivate nuclei, for implantation and incorporation of cell parts or individual cells into other cells or tissues or organisms, for microsurgery of minute vessels, muscular fibres and other tissues.

We claim:

1. A method for performing microoperations on cells, consisting in that a cell (29) is secured by means of a micro suction cup (5) and a microinstrument (1) is used to perforate the membrane of the cell (29), characterized in that the membrane of the cell (29) is perforated in a spot under the micro suction cup (5), the instrument (1) being introduced through the recess of the micro suction cup (5).

2. A method for performing microoperations on cells as claimed in claim 1, characterized in that the recess of the micro suction cup (5) is filled with an isotonic solution.

3. A device for performing microoperations on cells, comprising a microinstrument (1) installed in a holder (2) rigidly secured to a movable tip (3) of a three-way micromanipulator (4), and a micro suction cup (5) to secure a cell to be perforated, characterized in that the micro suction cup (5) is rigidly secured in the holder (2), the microinstrument (1) is located in the recess of the micro suction cup (5) coaxially therewith and is connected to the holder (2) by a means (7a and 7b) for reciprocating movement of the microinstrument (1) along the axis of the micro suction cup (5).

4. A device as claimed in claim 3, characterized in that the holder (2) is a hollow tee-joint (8) whose one pipe (9) communicates with the recess of the micro suction cup (5), an opposite pipe (10) houses a sealing ring (11) provides with a hole fitting the diameter of the microinstrument (1), while a third lateral pipe is equipped with a nipple to produce a negative pressure inside the recess of the micro suction cup (5) and provide an input for the isotonic solution.

5. A device as claimed in claim 3, characterized in that the means (7b) connecting the microinstrument (1) and the holder (2) is a lengthwise stepping mechanism.

6. A device as claimed in claim 3, characterized in that the means (7a) connecting the microinstrument (1) and the holder (2) is a diaphragm box whose casing (13) is rigidly secured to the holder (2), a diaphragm (15) is rigidly secured to the microinstrument (1), the chamber of said diaphragm box being communicated with a source of control pneumatic impulses.

* * * * *